US009940810B2

(12) United States Patent
Derenne et al.

(10) Patent No.: US 9,940,810 B2
(45) Date of Patent: Apr. 10, 2018

(54) PERSON SUPPORT APPARATUSES WITH PATIENT MOBILITY MONITORING

(71) Applicant: Stryker Corporation, Kalamazoo, MI (US)

(72) Inventors: Richard A Derenne, Portage, MI (US); Ammon K Wright, Portage, MI (US); Sean M Kirkwood, Portage, MI (US); Aaron Douglas Furman, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 14/928,513

(22) Filed: Oct. 30, 2015

(65) Prior Publication Data

US 2016/0140827 A1    May 19, 2016

Related U.S. Application Data

(60) Provisional application No. 62/081,723, filed on Nov. 19, 2014.

(51) Int. Cl.
| G08B 23/00 | (2006.01) |
| A61B 5/00 | (2006.01) |
| G08B 21/04 | (2006.01) |
| A61B 5/11 | (2006.01) |
| G08B 21/22 | (2006.01) |

(Continued)

(52) U.S. Cl.
CPC ........ *G08B 21/0446* (2013.01); *A61B 5/1117* (2013.01); *A61B 5/6892* (2013.01); *A61B 5/747* (2013.01); *G08B 21/043* (2013.01); *G08B 21/0461* (2013.01); *G08B 21/22* (2013.01); *A61B 2560/045* (2013.01); *A61B 2562/0252* (2013.01)

(58) Field of Classification Search
CPC .............. G08B 21/0446; G08B 21/043; G08B 21/0461; G08B 21/22; A61B 5/1117; A61B 5/6892; A61B 2560/045; A61B 2562/0252
USPC .......................................... 340/537.1, 573.7
See application file for complete search history.

(56) References Cited

U.S. PATENT DOCUMENTS

| 5,276,432 A | 1/1994 | Travis |
| 2006/0049936 A1* | 3/2006 | Collins, Jr. ........... A61B 5/1115 340/539.11 |
| 2008/0120784 A1 | 5/2008 | Warner et al. |

(Continued)

FOREIGN PATENT DOCUMENTS

WO    2012122002 A1    9/2012

*Primary Examiner* — Jack K Wang
(74) *Attorney, Agent, or Firm* — Warner Norcross + Judd LLP

(57) ABSTRACT

A person support apparatus, such as a bed, stretcher, cot, or the like, includes a fall detector. The fall detector is adapted to detect when a person associated with the person support apparatus has fallen and to issue a fall alarm. In some embodiments, the person support apparatus also includes an exit detection system that issues an exit alarm when the person exits from the person support apparatus. The fall alarm is given a higher priority than the exit alarm. The fall detector may include a camera, a thermal image sensor, a device worn by the person, or another sensor. The person support apparatus may also, or alternatively, include a timer for measuring how long an occupant remains out of the person support apparatus.

17 Claims, 6 Drawing Sheets

(51) Int. Cl.
G08B 1/08 (2006.01)
G06F 11/00 (2006.01)

(56) References Cited

U.S. PATENT DOCUMENTS

| | | | |
|---|---|---|---|
| 2008/0169931 A1* | 7/2008 | Gentry | A61B 5/1113 340/573.1 |
| 2011/0263950 A1* | 10/2011 | Larson | A61B 5/024 600/301 |
| 2014/0145848 A1* | 5/2014 | Amir | G08B 21/043 340/573.1 |
| 2015/0095054 A1* | 4/2015 | Kaigler | G06F 19/3418 705/2 |
| 2015/0112151 A1* | 4/2015 | Muhsin | A61B 5/002 600/301 |
| 2015/0323388 A1 | 11/2015 | Kostic et al. | |
| 2016/0106345 A1 | 4/2016 | Kostic et al. | |
| 2016/0275776 A1* | 9/2016 | Shen | G06F 19/345 |
| 2017/0231577 A1 | 8/2017 | Shalom et al. | |

* cited by examiner

Exit Event - Indication of a low priority alarm is indicated by yellow LED and audio indication.

Fall Event - Fall communicated from device on the patient to the chair. Indication of a medium priority alarm is indicated by amber LED and audio indication.

ated mobility monitoring system that monitors and analyzes the US 9,940,810 B2

PERSON SUPPORT APPARATUSES WITH PATIENT MOBILITY MONITORING

BACKGROUND

The present disclosure relates to person support apparatuses, such as beds, cots, stretchers, operating tables, chairs, or the like. More specifically, the present disclosure relates to person support apparatuses that include sensors for monitoring the motion of an occupant of the person support apparatus, including motion of the occupant when away from the person support apparatus.

SUMMARY

According to various embodiments, the present disclosure provides an improved person support apparatus having a mobility monitoring system that monitors and analyzes the movement of an occupant, such as a patient, while the patient is off the person support apparatus. This monitoring provides important data regarding the mobility and activity of a patient, and can be a useful indicator of the health and/or recovery of the patient. The mobility monitoring, in some embodiments, may tally the amount of time that the patient spends off a bed, chair, or other support. In other embodiments, the mobility monitoring includes monitoring more detailed aspects of the activity of the person while positioned off the bed, such as, but not limited to, the number of steps the person takes, the heart rate of the patient, the distance the person walks, and/or the locations the patient has traveled to. In still other embodiments, the mobility of the patient is monitored to determine whether a fall has occurred and to escalate an alarm when/if such a fall is detected.

According to one embodiment, a person support apparatus is provided that includes a support surface, an exit detector, a fall detection sensor, and a controller. The support surface is adapted to support a person thereon. The exit detector issues an alarm if the person exits the support surface. The fall detection sensor detects if the person falls. The controller is in communication with the exit detector and the fall detection sensor, and the controller is adapted to issue a first alarm if the person exits the support surface and to issue a second alarm if the person falls. The second alarm has a higher priority than the first alarm.

In at least one embodiment, the fall detection sensor comprises a receiver coupled to the person support apparatus and a portable unit worn by the person. The portable unit is in wireless communication with the receiver.

In another embodiment, the fall detection sensor comprises an image sensor adapted to detect images of the person after he or she exits from the person support apparatus. In some embodiments, the image sensor is a thermal image sensor.

The first alarm includes, in at least one embodiment, both a visual and an audio component. At least one of the audio and visual and components complies with standard 60601 of the International Electrotechnical Commission (IEC).

In some embodiments, the person support apparatus further includes a cable interface adapted to releasably couple to a cable of a nurse call system. The cable interface includes a plurality of electrical connectors, and the controller is adapted to open or close a first switch in communication with a first one of the electrical connectors when issuing the first alarm and to open or close a second switch in electrical communication with a second one of the electrical connectors when issuing the second alarm.

In other embodiments, the person support apparatus further includes a wireless interface adapted to wirelessly communicate with a local area network. The controller sends a first message to the local area network via the wireless interface when issuing the first alarm, and sends a second message to the local area network via the wireless interface when issuing the second alarm.

According to another embodiment, a person support apparatus system is provided that includes a first person support apparatus and a second person support apparatus. The first person support apparatus includes a first support surface, a first exit detector, and a first controller. The second person support apparatus includes a second support surface, a second fall detection sensor, and a second controller. The first person support apparatus is in communication with the second person support apparatus and the first controller is adapted to issue a first alarm if a person exits the first person support apparatus. The first controller is further adapted to issue a second alarm if the second fall detection sensor detects a fall of the person.

In other embodiments, the first person support apparatus further comprises a first fall detection sensor and the first controller is further adapted to issue the second alarm if the first fall detection sensor detects a fall of the person.

In some embodiments, the first person support apparatus is a bed and the second person support apparatus is a recliner.

The second controller issues the second alarm if the second fall detection sensor detects a fall of the person, in some embodiments. The second controller is further adapted to issue the first alarm if the first exit detector detects the person exiting the first person support apparatus.

In another embodiment, the second person support apparatus further comprises a second exit detector that is adapted to detect if the person exits the second person support apparatus. The first controller issues the first alarm if the second exit detector detects the person exiting the second person support apparatus.

In another embodiment, the first person support apparatus also includes a cable interface adapted to releasably couple to a cable of a nurse call system. The cable interface includes a plurality of electrical connectors, and the controller is adapted to open or close a first switch in communication with a first one of the electrical connectors when issuing the first alarm and to open or close a second switch in electrical communication with a second one of the electrical connectors when issuing the second alarm.

In other embodiments, the first person support apparatus further includes a first ID and the second person support apparatus further includes a second ID. The first person support apparatus is configured to transmit the first ID to the second person support apparatus and the second person support apparatus is configured to transmit the second ID to the first person support apparatus.

According to another embodiment, a person support apparatus is provided that includes a support surface, an exit detector, and a timer. The support surface is adapted to support a person thereon. The timer records how much time passes between when the person leaves the support surface and when the person returns to the support surface.

In other embodiments, the timer also records a time of day when the person leaves the support surface and/or a time of day when the person returns to the support surface.

The person support apparatus includes, in some embodiments, a controller that maintains a log of each time the person leaves the support surface and returns to the support surface. The log includes a time of day of when the person leaves the support surface and/or a time of day when the person returns to the support surface. A display is included in some embodiments of the person support apparatus that displays information from the log.

In another embodiment, the exit detector is adapted to be armed and disarmed, and to issue an alarm if the person exits the support surface while the exit detector is armed, and to not issue an alarm if the person exits the support surface while the exit detector is disarmed. The timer records how much time passes between when the person leaves the support surface and when the person returns to the support surface even when the exit detector is disarmed.

The person support apparatus includes a communication interface, in some embodiments, that forwards to an electronic medical records system a message of how much time passes between when the person leaves the support surface and when the person returns to the support surface.

In still other embodiments, the person support apparatus includes a communication interface adapted to communicate with a portable device worn by the person. The portable device monitors at least one of the following data items: how many steps the person takes; how far the person travels; the person's heart rate; how many calories the person burns; and how much time the person is non-stationary. The portable device communicates at least one of these data items to the person support apparatus. The person support apparatus may include a display adapted to display at least one of these data items.

According to another embodiment, a person support apparatus is provided that includes a support surface, an exit detector, and a timer. The support surface is adapted to support a person thereon. The exit detector is adapted to be armed and disarmed and to issue an alarm if the person exits the support surface while the exit detector is armed, and to not issue an alarm if the person exits the support surface while the exit detector is disarmed. The timer is in communication with the exit detector and is adapted to record how long the person remains off the support surface when the exit detector is disarmed.

In another embodiment, the timer is adapted to record how long the person remains off the support surface when the exit detector is armed.

The person support apparatus includes, in some embodiments, a controller adapted to maintain a log of each time the person is off the support surface and/or the time of day the person is off the support surface. The person support apparatus also includes, in at least some embodiments, a communication interface adapted to receive data from a second person support apparatus indicating an amount of time the person has remained off and/or on a second support surface of the second person support apparatus. The controller records this data from the second person support apparatus in the log.

In some embodiments, the person support apparatus further includes a communication interface adapted to communicate with a portable IV stand. The portable IV stand includes at least one sensor for monitoring at least one of the following data items: how many steps the person takes; how far the person travels; how many calories the person burns; and how much time the person is non-stationary. The portable IV stand communicates at least one of the data items to the person support apparatus.

According to still another embodiment, the person support apparatus includes a support surface adapted to support a person thereon, and a communication interface. The communication interface communicates with a portable IV stand and is adapted to receive at least one of the following data items from the portable IV stand: how many steps the person takes; how far the person travels; how many calories the person burns; and how much time the person is non-stationary. The person support apparatus includes a display adapted to display at least one of the data items.

In other embodiments, the person support apparatus includes an exit detector adapted to detect when the person leaves the support surface and when the person returns to the support surface, and the communication interface sends a message to the portable IV stand when the person leaves the support surface. The message indicates to the portable IV stand to begin monitoring at least one of the data items.

In some embodiments, the portable IV stand communicates with the communication interface via at least one of the following protocols: IEEE 802.11, IEEE 802.15.1, and IEEE 802.15.

According to another embodiment, a mobile IV stand is provided. The mobile IV stand includes a plurality of wheels, an IV pole having a hook adapted to support an IV bag, a communication interface, a sensor, and a controller. The sensor generates data indicative of a distance the mobile IV stand travels and the controller forwards the data to the communication interface.

In some embodiments, the IV stand includes a timer adapted to monitor how long the mobile IV stand is in motion. The IV stand may also include a sensor adapted to detect at least one of the following data items: how many steps a person associated with the mobile IV stand takes; how much time a person associated with the mobile IV stand remains standing next to the mobile IV stand; and a location of the mobile IV stand.

In some embodiments, the communication interface of the mobile IV stand is adapted to wirelessly communicate with a bed and/or an access point of a healthcare network.

In still another embodiment, the controller is further adapted to await receipt of a message from a person support apparatus before using the sensor to generate data indicative of the distance the mobile IV stand travels.

In any of the embodiments disclosed herein, the person support apparatus may be any one of a bed, stretcher, chair, recliner, and/or cot. In any of the embodiments disclosed herein having an exit detector, the exit detector may include a plurality of load cells positioned to support the support surface.

Before the various embodiments disclose herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
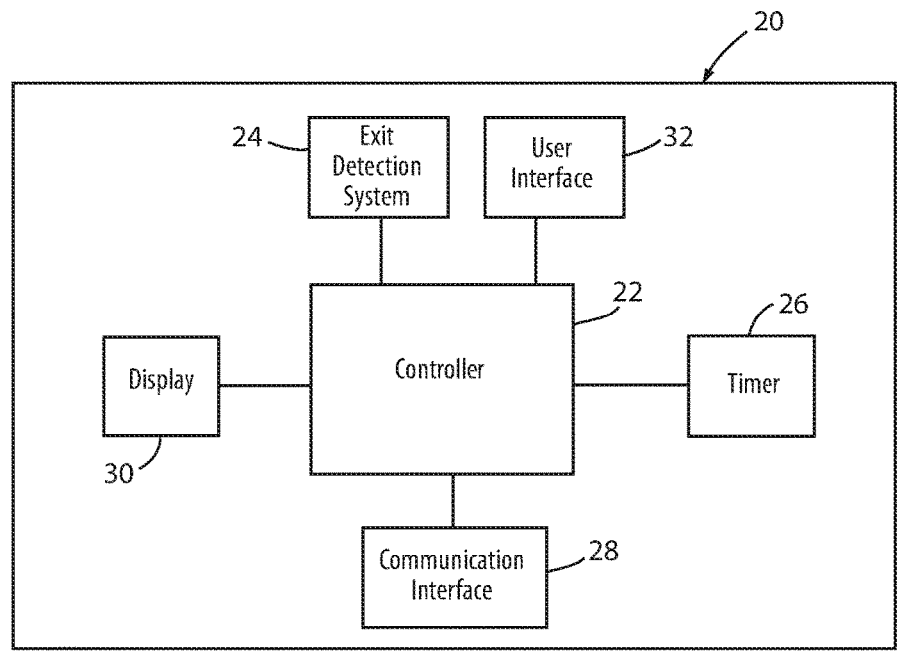
FIG. 1 is a diagram of a person support apparatus according to one embodiment of the disclosure.
Figure 8:
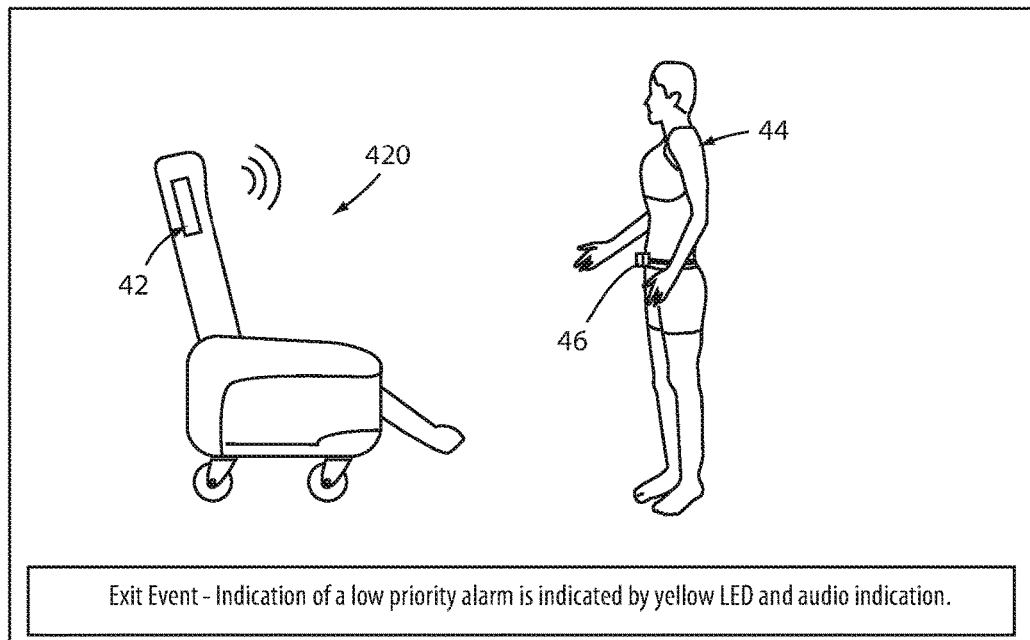
FIG. 8 is a side elevation diagram of a person support apparatus according to yet another embodiment shown in an alarm condition of a first priority.
Figure 9:
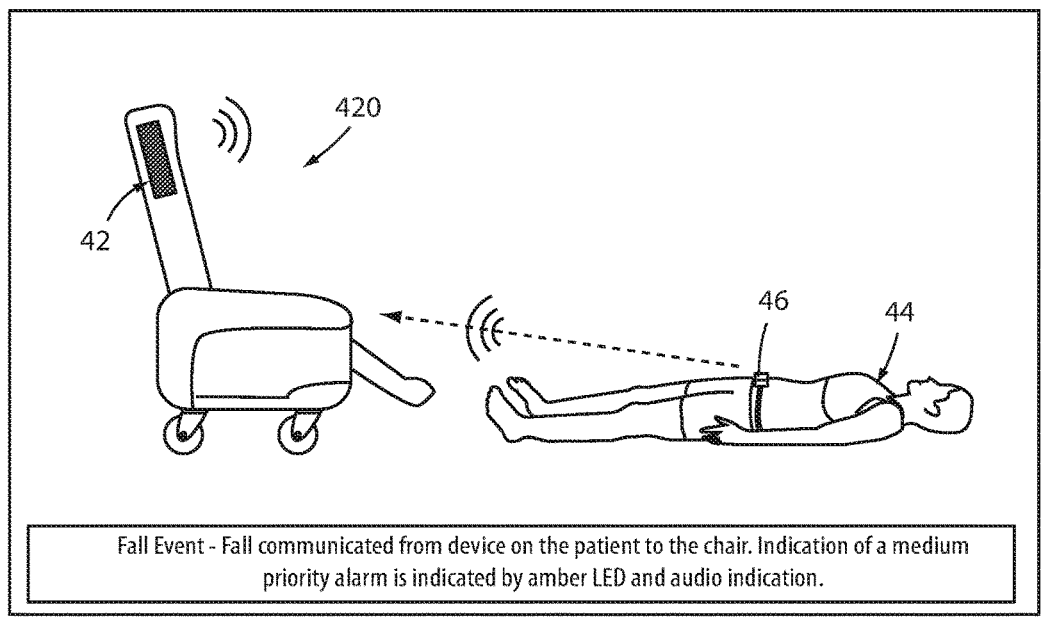
FIG. 9 is a side elevation diagram of the person support apparatus of FIG. 8 shown in an alarm condition of a second priority that is higher than the first priority.
Figure 11:
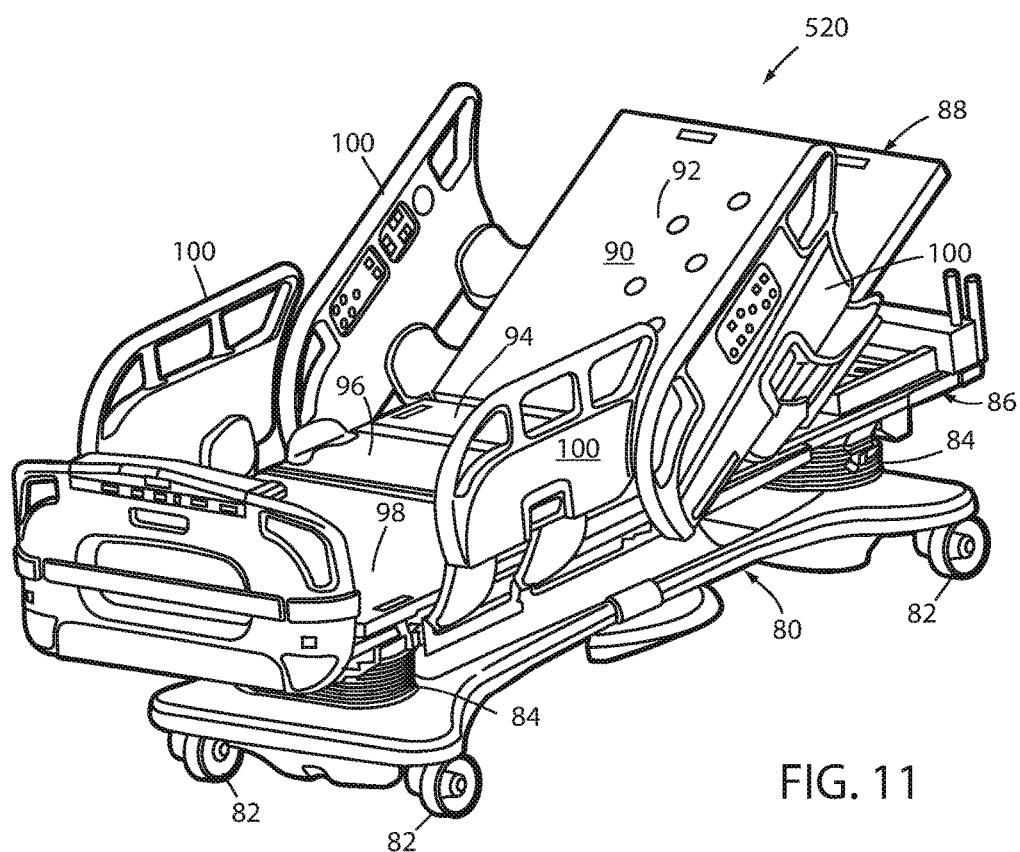
FIG. 11 is a plan view diagram of another person support apparatus that may incorporate any one or more aspects of the various embodiments disclosed herein.

A person support apparatus 20 according to one embodiment is shown in diagrammatic form in FIG. 1. It will be understood by those skilled in the art that the physical construction of person support apparatus 20 can take on a variety of different forms, including, but not limited to, those of a cot, a stretcher, a gurney, a recliner, an operating table, a residential bed, or any other structure capable of supporting a person, whether stationary or mobile and/or whether medical or residential. For example, FIGS. 8-9 illustrate a person support apparatus 420 that is implemented as a recliner, and FIG. 11 illustrates a person support apparatus 520 that is implemented as a hospital bed.

In the embodiment of person support apparatus 20 shown in diagrammatic form in FIG. 1, much of the physical construction of person support apparatus 20 has been omitted. It will be understood that person support apparatus 20 may include any one or more of the components shown in either or both of person support apparatus 420 (FIGS. 8-9) and/or person support apparatus 520 (FIG. 11), or components from still other types of person support apparatuses.

Person support apparatus 20 includes a controller 22, an exit detection system 24, a timer 26, a communication interface 28, a display 30, and a user interface 32. Controller 22 is constructed of any electrical component, or group of electrical components, that are capable of carrying out the functions described herein. In many embodiments, controller 22 is a conventional microcontroller, although not all such embodiments need include a microcontroller. In general, controller 22 includes any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 22 in carrying out the functions described herein, as well as the data necessary for carrying out these functions, are stored in a memory (not labeled) accessible to controller 22.

Controller 58 is also in communication with user interface 32. User interface 32 includes a plurality of controls—which may be buttons, dials, switches, or other devices—that allow a user to control various aspects of person support apparatus 20, including, but not limited to, exit detection system 24, communication interface 28, and display 30. In one embodiment, user interface 32 includes a control that enables a user to turn exit detection system 24 on and off, as will be discussed in greater detail below.

Exit detection system 24 includes any one or more transducers and/or sensors that are adapted to detect when an occupant of person support apparatus 20 exits person support apparatus 20. The form of exit detection system 24 can vary widely in different embodiments of person support apparatus 20. In one embodiment, exit detection system 24 includes an array of pressure sensors that is laid on top of, or integrated into, a mattress (not shown) positioned on person support apparatus 20 (if person support apparatus 20 is a bed, cot, or stretcher) or that is laid on top of, or integrated into a cushion on person support apparatus 20 (if person support apparatus 20 is a chair, recliner, or the like). Such a pressure sensing array is constructed, in at least one embodiment, in any of the manners disclosed in commonly assigned U.S. patent application Ser. No. 14/003,157 filed Oct. 14, 2013 by inventors Joshua Mix et al. and entitled SENSING SYSTEM FOR PATIENT SUPPORTS; or in any of the manners disclosed in commonly assigned U.S. patent application Ser. No. 14/019,089 filed Sep. 5, 2013 by inventor Geoffrey Taylor and entitled ADAPTIVE CUSHION METHOD AND APPARATUS FOR MINIMIZING FORCE CONCENTRATIONS ON A HUMAN BODY, the complete disclosure of both of which are incorporated herein by reference.

In another embodiment, exit detection system 24 is constructed to include one or more infrared sensors that detect and process thermal images of the occupant of person support apparatus 20 in order to determine the position and movement of the occupant. For example, in at least one embodiment, exit detection system 24 is constructed in any of the manners disclosed in commonly assigned U.S. patent application Ser. No. 61/989,243 filed May 6, 2014 by inventors Marko Kostic et al. and entitled PERSON SUPPORT APPARATUS WITH POSITION MONITORING, the complete disclosure of which is also incorporated herein by reference.

In still other embodiments, exit detection system 24 is constructed to include a plurality of force sensors, such as, but not limited to, load cells that detect a weight and/or movement of an occupant of person support apparatus 20 while the occupant remains thereon. One example of such a system is disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference.

In still other embodiments, exit detection system 24 includes one or more video cameras that monitor the position of an occupant of person support apparatus 20 and visually detect whether/when the occupant exits person support apparatus 20. One such video-based system is disclosed in commonly assigned U.S. patent application Ser.

No. 13/242,022 filed Sep. 23, 2011 by inventors Richard Derenne et al. and entitled VIDEO MONITORING SYSTEM, the complete disclosure of which is also incorporated herein by reference.

Regardless of its specific components and/or arrangement, person support apparatus 20 is configured to determine a mobility time of its occupant. The mobility time is the amount of time that the occupant spends off person support apparatus 20. As will be discussed in greater detail below, the mobility time may be further refined to exclude the amount of time that the occupant spends off person support apparatus 20 while seated, or otherwise positioned, on a second person support apparatus, or some other structure that the occupant can sit or lie on. Thus, the mobility time provides an indication of the amount of time that the occupant has spent walking and/or standing.

The mobility time can be useful in assessing how mobile a particular individual, such as a patient in a hospital is, as well as how much physical activity the patient is undergoing. In many instances, patient activity, such as walking, is believed to help facilitate recovery for the patient. By monitoring how much time the patient spends off person support apparatus 20, person support apparatus 20 is able to provide useful information to the caregivers associated with that patient.

Controller 22 of person support apparatus 20 is configured to start timer 26 when controller 22 receives information from exit detection system 24 indicating that the occupant has left person support apparatus 20. The timer 26 is a clock, in at least one embodiment, that enables controller 22 to not only monitor the total amount of time the occupant spends away from person support apparatus 20, but also to time stamp the moment the occupant leaves and/or the moment the occupant returns to person support apparatus 20. That is, timer 26, in at least one embodiment, not only keeps track of the amount of time that passes between the occupant's departure from, and return to, person support apparatus 20, but it also keeps track of the time of day of each departure and return. All of this information is recorded in a memory (not shown) on person support apparatus 20 and/or, in at least some embodiments, forwarded off of person support apparatus 20 to another entity, such as an electronic medical records (EMR) system 34.

Figure 2:
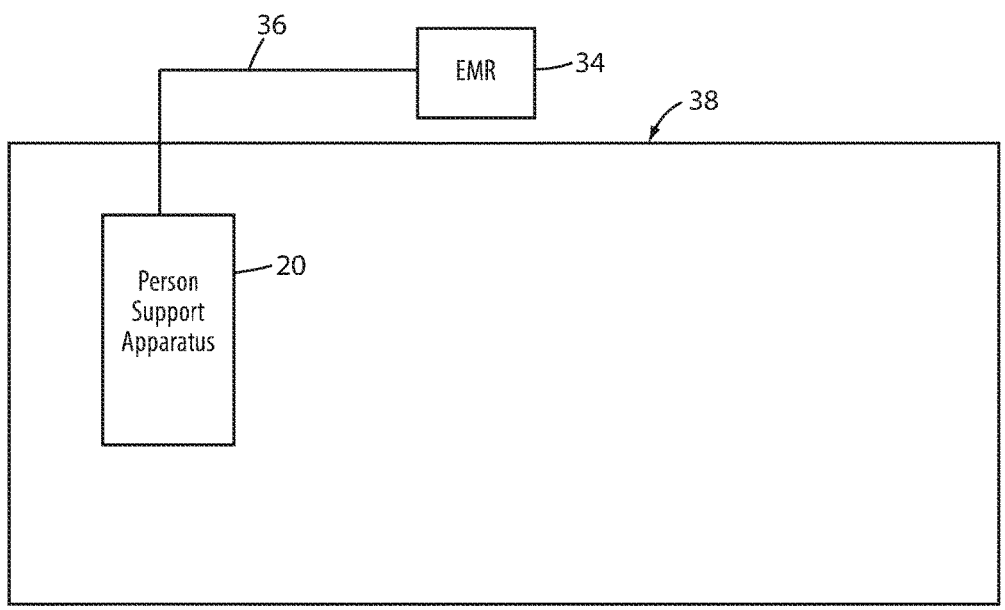
FIG. 2 is a plan view diagram of the person support apparatus of FIG. 1 illustrated in a room.

More specifically, FIG. 2 illustrates person support apparatus 20 positioned in a room 38 and in communication with an EMR system 34 via a communication link 36. Communication link 36 couples to communication interface 28 of person support apparatus 20. Communication interface 28 includes, in at least one embodiment, a wireless transceiver and communication link 36 is a wireless communication link between this transceiver and another wireless transceiver positioned within range of person support apparatus 20. This other wireless transceiver is, in some embodiments, part of a wireless access point to a local area network, such as a local area network of a medical facility. In at least some embodiments, wireless communication link 36 is a WiFi (IEEE 802.01) link. In other embodiments, different types of wireless links may be used, such as, but not limited to, ZigBee, Bluetooth, etc. In still other embodiments, communication link 36 comprises one or more cables that couple person support apparatus 20 to EMR system 34.

Regardless of the structure of communication link 36, user interface 32 includes one or more controls that allow a user to transfer the aforementioned data log stored on person support apparatus 20 to EMR system 34. That is, in response to user manipulation of one or more controls on user interface 32, controller 22 sends the data log, or portions of the data log, to EMR system 34. The specific content of the data log may vary, but typically includes one or more of the following: the occupant's total time away from person support apparatus 20, each departure time of the occupant from person support apparatus 20, each return time of the occupant from person support apparatus 20, the length of each trip the occupant took away from person support apparatus 20, and/or the total amount of time that the occupant has spent occupying person support apparatus 20. This latter data item provides a tool for comparing how much time the occupant spends on person support apparatus 20 versus how much time he or she spends off person support apparatus 20.

Although FIG. 2 illustrates person support apparatus 20 in communication with EMR system 34, it will be understood that person support apparatus 20 does not need to—and indeed is not configured to do so in at least some embodiments—transmit the log data to an EMR system. In some embodiments, person support apparatus 20 merely makes all or a portion of the data log available for display on display 30 of person support apparatus 20. In still other embodiments, person support apparatus 20 is configured to both display the log data (or portions of it) locally and to transfer it to EMR system 34.

User interface 32 of person support apparatus 20 further includes at least one control that allows a user to clear the log data from the memory on board person support apparatus 20. This enables the user to clear old information, such as when a new patient is assigned to that particular person support apparatus.

In some embodiments of person support apparatus 20, exit detection system 24 is adapted to be able to also, or alternatively, issue an alarm when the occupant exits. In such embodiments, user interface 32 is adapted to allow a user to choose whether the detection of the occupant's departure triggers timer 26, an alarm, neither, or both. Thus, in some situations, if a user wants to be alerted of the occupant's departure from person support apparatus 20, but is not interested in recording how much time the user spends off person support apparatus 20, the user can use user interface 32 to cause controller 22 to issue an alarm (audio and/or visual) when the occupant departs, but not start timer 26. In other situations, if the user does not want to be alerted to the occupant's departure, but does wish to record the amount of time the occupant spends out of the person support apparatus, the user can use user interface 32 to cause controller 22 to start timer 26 when the occupant departs, but not trigger any alarm. Similarly, if the user wants controller 22 to both start timer 26 and to issue an alarm when the occupant departs, he or she can do this via user interface 32. Finally, if the user does not wish to record the amount of time the occupant is away from person support apparatus 20, nor does the user wish to be alerted of the occupant's departure, the user can use user interface 32 to instruct controller 22 to neither issue an alarm nor start timer 26 when the occupant's departure is detected.

Figure 3:
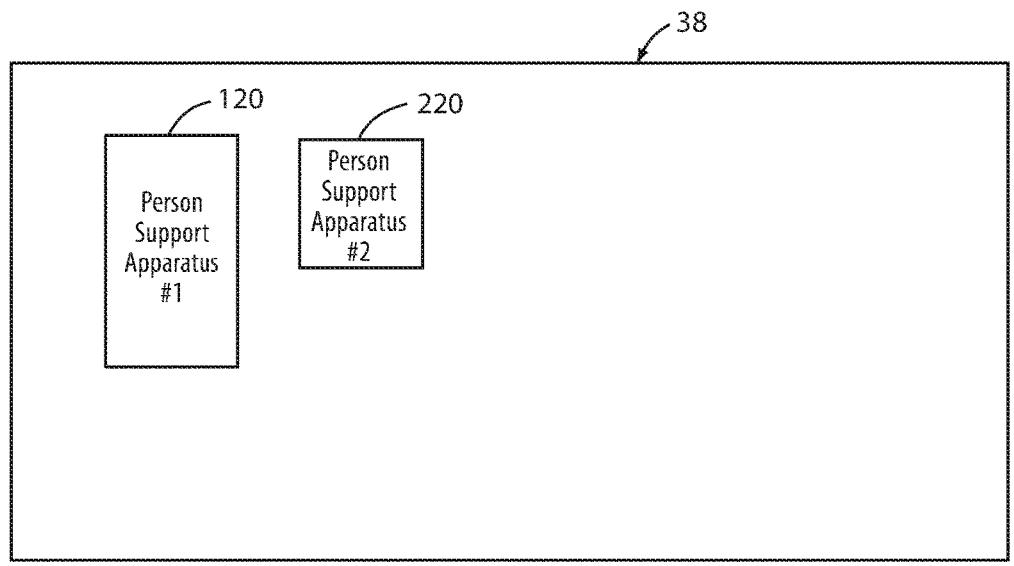
FIG. 3 is a plan view diagram of another embodiment of a person support apparatus shown in a room with a second person support apparatus.

FIG. 3 illustrates a modified first person support apparatus 120 positioned in a room 38 in which a modified second person support apparatus 220 is also positioned. Both first and second person support apparatuses 120 and 220 include the components of person support apparatus 20 shown in FIG. 1. However, first and second person support apparatuses 120 and 220 differ from person support apparatus 20 in the construction of communication interface 28 and the programming of controller 22. More specifically, first and second person support apparatuses 120 and 220 include a controller 22 and a communication interface 28 that are configured to allow them to communicate with each other. That is, first person support apparatus 120 is adapted to communicate with second person support apparatus 220, and vice versa. Communication interfaces 28 for each person support apparatus 120 and 220 include transceivers, in at least some embodiments, that communicate using any of the 802 standards of the Institute of Electrical and Electronics Engineers (IEEE), such as, but not limited to, 802.11 (WiFi), 802.15.1 (Bluetooth), and/or 802.15.4 (ZigBee). Other communication protocols may alternatively be used, including a cable connection between person support apparatuses 120 and 220.

First person support apparatus 220 is adapted to transmit to second person support apparatus 220 data indicating whether or not the occupant of first person support apparatus 120, after having exited first person support apparatus 120, has taken a seat, or otherwise supported himself or herself, on second person support apparatus 220. First person support apparatus 120 uses this data to determine how much time its occupant is away and not seated on second person support apparatus 220. In other words, first person support apparatus 120 performs the same timing function as person support apparatus 20 that yields a total amount of time the occupant is gone, but subtracts from this time an amount of time that the occupant spends on person support apparatus 220.

For example, if the occupant of first person support apparatus 120 leaves for 45 minutes, first person support apparatus 120 detects and measures this time period using exit detection system 24, timer 26, and controller 22. Suppose further that, during those forty-five minutes that the occupant is away from first person support apparatus 120, the occupant sits on second person support apparatus 220 for twenty minutes. Second person support apparatus 220 detects these twenty minutes using its exit detection system 24 and timer 26 and communicates this to first person support apparatus 120. First person support apparatus 120 then subtracts the twenty minutes from the forty-five minutes it measured to yield a value of twenty-five minutes. This twenty-five minute value is recorded, logged, and/or displayed in any of the manners discussed above with respect to person support apparatus 20, including, but not limited to, transmitting it via a communication link 36 (not shown in FIG. 3) to an EMR system 34.

The twenty-five minutes computed by first person support apparatus 120 in this example is an indication of how long the occupant is not only away from first person support apparatus 120, but how much of that time the occupant spent standing and/or walking. This can be especially helpful in a medical facility setting where it is desirable to keep track of the mobility of a patient and/or how much exercise or movement the patient is achieving. By having first person support apparatus 120 communicate with second person support apparatus 220, a more accurate measurement of the amount of time the patient has been mobile can be generated by removing from the measurement time which the patient spends sitting or lying on another person support apparatus. In some medical facility embodiments, first person support apparatus 120 is a bed while second person support apparatus 220 is a nearby chair or recliner. The mobility time of the patient that is calculated by the bed therefore excludes any time that the patient has spent sitting on the chair or recliner.

Although first second person support apparatus 120 has been described herein as calculating the mobility time of its occupant by subtracting from the total away time of its occupant any time spent on second person support apparatus 220, it will be understood that the opposite can occur. That is, second person support apparatus 220, in some embodiments, calculates the mobility time of its occupant by subtracting from the exit time of its occupant any time spent on first person support apparatus 120. In still other embodiments, both first and second person support apparatuses 120 and 220 each calculate their own mobility time of the occupant by subtracting from their respective total occupant away times any time spent on the other person support apparatus. Each person support apparatus makes this time available for display, or sends to the other person support apparatus for comparison purposes.

The manner in which the mobility time of an occupant is computed can vary widely, depending upon the implementation of exit detection system 24 in the person support apparatuses 120 and 220. If exit detection system 24 is an image based system, such as the video system disclosed in the aforementioned Ser. No. 13/242,022 patent application, the video exit detection system 24 sends a signal to first person support apparatus 120 when the occupant leaves. This causes controller 22 to start timer 26. When the video exit detection system 24 detects that the occupant has moved onto another person support apparatus, such as second person support apparatus 220, the video exit detection system 24 sends another signal to controller 22 indicating this fact, and controller 22 responds by halting timer 26. When video exit detection system 24 detects the occupant leaving second person support apparatus 220, it sends another signal to controller 22 that causes controller 22 to re-start timer 26. This continues until the occupant eventually returns to first person support apparatus 120, at which point the video exit detection system 24 sends a signal to controller 22 causing controller 22 to stop timer 26. The total amount of time on timer 26 at that point provides an indication of the mobility time of the patient for that particular trip off person support apparatus 120. This data is stored and logged, and timer 26 is then reset for any subsequent trips off person support apparatus 120.

If exit detection system 24 is implemented in a manner in which the location of a particular occupant cannot be tracked between first and second person support apparatuses 120 and 220, unlike a video exit detection system, the computation of the occupant's mobility time can be calculated in a different manner. For example, if exit detection system 24 of both person support apparatuses 120 and 220 comprises one or more force sensors that detect the weight (or absence thereof) of the occupant on the person support apparatus, each person support apparatus sends a patient exit message to the other person support apparatus when it detects that its occupant has departed. The patient exit message includes one or more of the following: an indication of the occupant's exit, the time of exit, an ID of the transmitting person support apparatus, an ID associated with the patient who has exited, and/or a weight of the patient who has exited. The exiting of the patient also triggers controller 22 to start timer 26.

After the patient exit message has been sent and timer 26 started, the associated controller continues to operate timer 26 until it receives a patient entry message (transmitted via communication interfaces 28) indicating the entry of the patient onto the other person support apparatus. This patient entry message may include any one or more of the following data: an indication of the occupant's entry, the time of the entry, an ID of the transmitting person support apparatus, an ID associated with the patient who has entered, and/or a weight of the patient who has entered. When the first person support apparatus receives this patient entry message, it stops its timer until it receives a patient exit message from the other person support apparatus. When that patient exit message is received, it re-starts its timer 26 until the occupant either returns, or re-enters another person support apparatus 20 (at which point it receives another patient entry message). When the patient finally returns, the time on the timer indicates how much time the patient has spent away from the person support apparatus while not being supported on the other person support apparatus. This time is stored and logged and/or transmitted elsewhere, as noted above.

In embodiments of person support apparatuses 120 and 220 where its exit detection system 24 detects the weight or absence of weight of their occupants, controller 22 may be further programmed to follow additional steps to help distinguish the movement of an exiting occupant from the movement of other individuals, such as, but not limited to, visitors in a medical setting. Thus, for example, if a patient on a first person support apparatus 120 exits therefrom and, while so exited, receives a visitor who sits on second person support apparatus 220, first person support apparatus 120 is configured to keep running timer 26 in such a situation because it is the visitor, not the occupant of first person support apparatus 120, who has entered second person support apparatus 220. Controller 22 of first person support apparatus 120 knows to keep running timer 26 in this situation because it compares the patient's weight, transmitted in the patient entry message, with the weight of its occupant, which it has stored in memory. If the two don't match within a specified tolerance, controller 22 determines that the patient entry message it receives corresponds to another individual, and not the patient it is associated with, and therefore does not stop timer 26 in this situation.

If the visitor and the patient have substantially the same weight, controller 22 of the first person support apparatus 120 will re-start its timer 26 when it receives the patient entry message from the second person support apparatus 220, despite the fact that this corresponds to the visitor, and not the patient, entering thereon. If the patient returns to first person support apparatus 120 before the visitor exits second person support apparatus 220, however, then controller 22 of first person support apparatus 120 will know that the previously received patient entry message from second person support apparatus 220 did not correspond to the patient, but instead corresponded to someone else (i.e. the visitor). In that case, controller 22 of first person support apparatus 120 will add back to the time value on timer 26 the amount of time since it received the patient entry message from second person support apparatus 220 (which corresponded to the visitor). This time amount is determined by controller 22, in at least some embodiments, by programming controller 22 to record the absolute times at which it receives any patient entry messages.

In those rare situations where the visitor and the patient are of the same weight, and the visitor both enters second person support apparatus 220 subsequent to the patient exiting first person support apparatus 120 and leaves second person support apparatus 220 before the patient returns to first person support apparatus 120, controller 22 may end up computing an inaccurate patient mobility time value unless additional measures are taken. Such additional measures may take on a variety of different forms. In at least some embodiments, each patient is assigned a wristband or other device having a unique ID in it that is readable by an adjacent wireless device (e.g. a near field ID tag readable by a near field reader, or the like). Each person support apparatus 120 and 220 includes a reader that is able to read the data associated with the wristband, or other device, and determine the identity of its occupant. This information is communicated in the patient entry and patient exit messages that are sent, thereby enabling an accurate mobility time of the patient to be computed by one or both of the person support apparatuses 120 and/or 220.

In still other embodiments, person support apparatuses 120 and/or 220 are in communication with one or more additional sensors that detect when a patient has sat on, or otherwise rested on, another object or device. For example, in one embodiment, person support apparatuses 120 and/or 220 are in communication with a sensor that detects the usage of a toilet or commode by the patient. Such a sensor can be a conventional pressure transducer that detects the weight exerted by the patient on the toilet seat, or it may take on other forms. The sensor sends toilet entry and toilet exit messages similar to the patient entry and patient exit messages sent by first and second person support apparatuses 120 and 220. First and second person support apparatuses 120 and 220 also react to these toilet entry and toilet exit messages in a similar manner. That is, they subtract from the occupant's total mobility time any time spent sitting on the toilet.

Person support apparatuses 120 and/or 220 are, in at least some embodiments, associated with each other. That is, they contain data indicating that they are assigned to the same patient, or are otherwise intended to be associated with the same patient. This data is used by person support apparatuses 120 and/or 220, in at least some embodiments, to distinguish patient entry and patient exit messages that are sent by person support apparatuses 120 and 220 from similar messages that are sent by other person support apparatuses that may be within communication range of person support apparatuses 120 and/or 220. Thus, for example, if first person support apparatus 120 is a first bed, and second person support apparatus 220 is a first recliner, and they are both positioned in a room having a second bed and a second recliner, such association data allows first and second person support apparatuses 120 and 220 to distinguish between the messages they send and any messages that may be sent by the second bed and second recliner. In this manner, first and second person support apparatuses 120 and 220 ignore any patient entry and/or patient exit messages that come from the second bed or second recliner, and vice versa. This is done because a patient will typically not exit his or her bed and sit on the chair or recliner positioned adjacent to his or her roommate's bed, but instead will sit on the chair or recliner positioned adjacent to his or her own bed. Of course, if exit detection system 24 of person support apparatuses 120 and/or 220 utilizes a video system, or otherwise uses devices that can individually identify patients (e.g. ID tags or the like), first and second person support apparatuses 120 and/or 220 will process patient entry and patient exit messages from any person support apparatus in which their specific patient enters or exits, regardless of whether or not the person support apparatus he or she enters is intended for him or her, or for his or her roommate.

The association of first person support apparatus 120 and second person support apparatus 220, if done, can be accomplished in different manners. In one embodiment, this is done manually by a user through the use of user interface 32 in one or both of the support apparatuses. In other embodiments, such association is accomplished automatically, or semi-automatically, in any of the manners disclosed in commonly assigned U.S. patent application Ser. No. 13/802, 992 filed Mar. 14, 2013 by inventors Michael Joseph Hayes et al. and entitled COMMUNICATION SYSTEMS FOR PATIENT SUPPORT APPARATUSES, the complete disclosure of which is hereby incorporated herein by reference.

Figure 4:
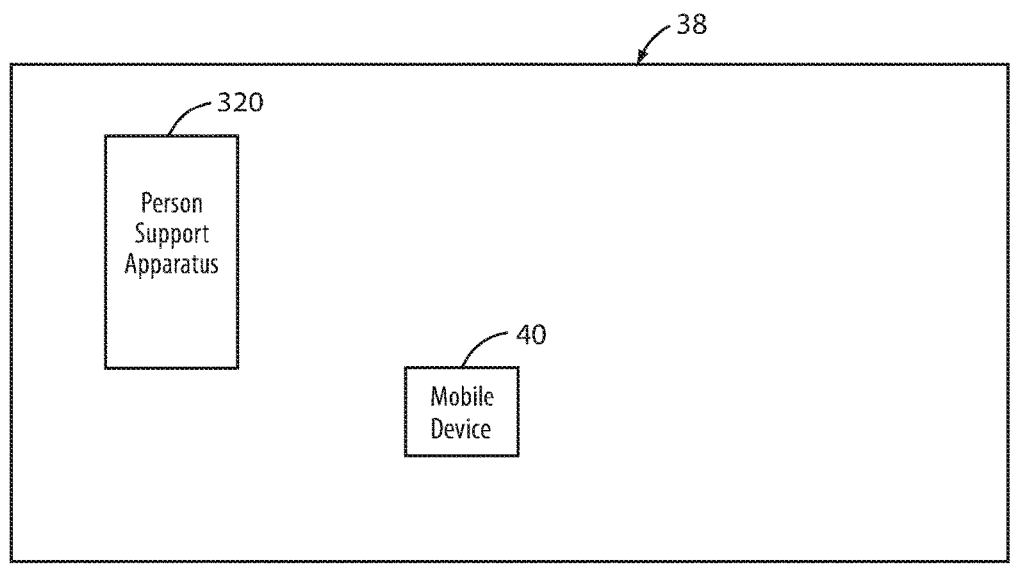
FIG. 4 is a plan view diagram of another embodiment of a person support apparatus illustrated in a room with a mobile device that communicates with the person support apparatus.

FIG. 4 illustrates a modified person support apparatus 320 positioned in a room 38 in which a mobile device 40 is also positioned. Person support apparatus 320 includes the same components of person support apparatus 20 shown in FIG. 1. However, person support apparatus 320 differs from person support apparatus 20 in the construction of communication interface 28 and the programming of controller 22. More specifically, person support apparatus 320 includes a controller 22 and a communication interface 28 that are configured to allow person support apparatus 320 to communicate with mobile device 40. Communication interface 28 for person support apparatus 320 includes at least one transceiver, in some embodiments, that communicates using any of the 802 standards of the Institute of Electrical and Electronics Engineers (IEEE), such as, but not limited to, 802.11 (WiFi), 802.15.1 (Bluetooth), and/or 802.15.4 (ZigBee). Other communication protocols may alternatively be used, including a cable connection between person support apparatus 320 and mobile device 40.

In one embodiment, mobile device 40 is an activity tracker that is adapted to be worn by the occupant of person support apparatus 320. The activity tracker can take on a wide variety of different forms. In one embodiment, the activity is any one of the Fitbit activity trackers marketed by Fitbit, Inc. of San Francisco, Calif. In other embodiments, mobility device 40 is any one of the following: a Vivofit fitness band marketed by Garmin International, Inc. of Olathe, Kans.; a Microsoft Band smart watch marketed by Microsoft Corporation of Redmond, Wash.; a Nike+ Fuelband marketed by Nike, Inc. of Beaverton, Oreg.; a Gear Fit wristband marketed by Samsung of Suwon, South Korean; an Up or UP24 wristband marketed by Jawbone, of San Francisco, Calif.; or an Apple iWatch marketed by Apple Inc. of Cupertino, Calif. In still other embodiments, mobile device 40 is still another type of activity tracker. Still further, in some embodiments, the activity tracker includes one or more sensors (e.g. accelerometers) that are adapted to detect whether or not the individual wearing the tracker has fallen, and to transmit a message in the event of such a fall occurrence, as will be discussed in greater detail below.

Regardless of the specific brand, type, model, or configuration of the activity tracker, person support apparatus 320 includes at least one communication interface 28 that is adapted to communicate with the activity tracker. Controller 22 receives data from the activity tracker indicating how far the occupant of person support apparatus 320 has walked, his or her heart rate, the estimated number of calories burned, and/or any other data that is measured by the activity tracker. Controller 22 records and logs this data, makes it available for display on display 30, and/or transmits it to a remote location, such as, but not limited to, EMR system 34. Caregivers associated with the occupant of person support apparatus 320 therefore are provided with information regarding the activity level of that occupant, which may be helpful in assessing the condition and/or recovery of that occupant.

In some embodiments, person support apparatus 320 is also adapted to calculate a mobility time of its occupant in the same manner discussed above. That is, in addition to communicating with an activity tracker, person support apparatus 320, in at least some embodiments, includes the same programming and/or configurations discussed above with respect to person support apparatuses 120 and/or 220. When thus configured, person support apparatus 320 may include multiple transceivers in its communication interface 28—one for other person support apparatuses and one for the activity tracker. Alternatively, both the other person support apparatuses and the activity tracker may utilize a common communication protocol, in which case communication interface 28 need only include a single type of transceiver.

The particular activity tracker worn by a patient is associated with a specific person support apparatus 320, in at least one embodiment, by a caregiver manually associating an ID of that activity tracker with a specific person support apparatus 320. That is, in at least one embodiment, a caregiver manually enters a unique ID of a specific activity tracker into the person support apparatus 320 that will support that particular patient. This is done via user interface 32. In other embodiments, person support apparatus 320 and its corresponding activity tracker may be associated automatically, or semi-automatically, using other means, such as including one or more sensors on person support apparatus 320 that automatically detect the nearby presence of the activity tracker and, based on that presence, carry out an automatic or semi-automatic association process. Once an activity tracker is associated with a specific person support apparatus 320, any messages that either one receives from other activity trackers or other person support apparatuses are ignored, and vice versa, thereby ensuring that, for example, the activity data of a patient and his or her roommate do not get mixed together.

Figure 5:
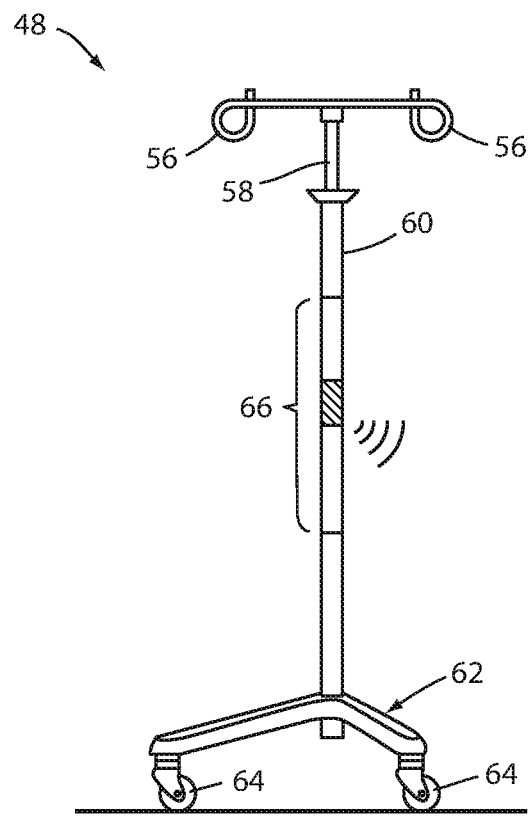
FIG. 5 is a side elevation view of the mobile device of FIG. 4 implemented as a mobile IV stand.

In some alternative embodiments, mobile device 40 is a mobile IV stand rather than an activity tracker. FIG. 5 illustrates one example of a type of mobile IV stand 48 that mobile device 40 is implemented as in at least one embodiment. Mobile IV stand 48 includes a plurality of hooks 56 that are adapted to support an IV bag having an IV line that is coupled to the patient. Hooks 56 are secured to a top end of a pole extension 58 that is slidable vertically within a pole 60 so as to be positionable at different heights. Pole 60 is supported on a base 62 having a plurality of wheels 64 that enable mobile IV stand 48 to be wheeled alongside a patient to different locations. In some embodiments, pole 60 supports an IV pole topper of the type disclosed in commonly assigned U.S. patent application Ser. No. 13/686,243 filed Nov. 27, 2012 by inventors Michael Graves et al. and entitled POLE AND TOPPER FOR MOBILE MEDICAL DEVICE, the complete disclosure of which is hereby incorporated herein by reference.

Figure 6:
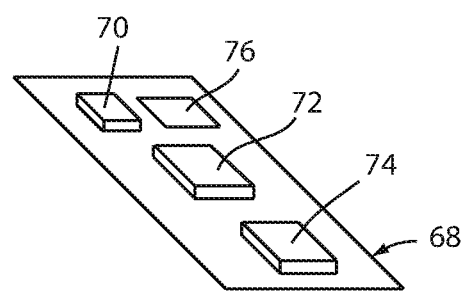
FIG. 6 is a perspective view of one embodiment of a control board used with the mobile IV stand of FIG. 5.

Mobile IV stand 48 further includes a sensing unit 66 that is built into, or otherwise coupled to, pole 60. Sensing unit 66 is in communication with a control board 68 (FIG. 6) that is housed inside of pole 60, positioned at base 62, or otherwise coupled to mobile IV stand 48. Control board 68 includes a plurality of electronic components mounted thereon, such as one or more accelerometers 70, a heart rate sensor 72, a microcontroller 74, and a transceiver 76, which may be a Bluetooth transceiver or another type of transceiver that is adapted to wirelessly communicate with person support apparatus 320. Accelerometer(s) 70 are adapted to detect the acceleration of mobile IV stand 48 as it is wheeled around room 38 or elsewhere. Controller 22 processes this acceleration data to determine a distance traveled and, in some embodiments, a path of the travel. In other embodiments, accelerometers 70 are replaced with one or more wheel encoders that are coupled to one or more wheels 64 of mobile IV stand 48 and that measure the number of rotations of the wheels 64. In still other embodiments, still other sensors are used to sense the movement of mobile IV stand 48.

Heart rate sensor 72, in one embodiment, is a conventional touch sensor that detects a patient's pulse whenever he or she grips any of the surface of pole 60 in which sensing unit 66 is implemented. Such touch pulse sensors are known in the art and commonly found in treadmills, and other exercise equipment. Heart rate sensor 72 is in electrical communication with microcontroller 74 which calculates the patient's heart rate when he or she grips the area of sensing unit 66 and stores this calculated heart rate.

The information gathered by mobile IV stand provides a caregiver associated with a patient information about the mobility of the patient that assists in prescriptive activities for helping the patient to a speedy recovery. The data gathered by mobile IV stand 48 provides, in at least one embodiment, a time history of the patient's heart rate for each walking session as well as statistical information for the various metrics measured by mobile IV stand 48 (e.g. distance traveled). In some embodiments, the patient activates mobile IV stand 48's sensors based upon any one or more of the following: the detection of the patient's heart rate by the heart rate sensor 72, the movement of mobile IV stand 48 (as sensed by accelerometers 70 or other sensors), the receipt of a message from person support apparatus 320 (e.g. a message indicating the patient has exited therefrom); and/or the activation of a switch on mobile IV stand 48.

Transceiver 76 communicates with communication interface 28 of person support apparatus 320 and transmits thereto the data gathered by the sensors on board mobile IV stand 48. The transmitted data includes any one or more of the following: the distance mobile IV stand 48 travels; the speeds of mobile IV stand 48; the time the patient began and/or ended each trip away from person support apparatus 320 accompanied by mobile IV stand 48; and/or the locations the patient travels to with mobile IV stand 48. This data is stored, logged, made available for display on display 30 of person support apparatus 320, and/or transmitted to one or more remote computer devices, such as, but not limited to, EMR system 34.

In still other embodiments, mobile IV stand 48 is adapted to communicate the data it gathers from it sensors directly to another device other than person support apparatus 320. For example, in one embodiment, the mobile IV stand is adapted to transmit the information it gathers to a computer network of a healthcare facility. The computer network may be in communication with EMR system 34. Alternatively, the mobile IV stand may directly communicate with the EMR system, or some other system or device of the healthcare facility.

In one embodiment, the transmission of data from the mobile IV stand 48 to either the person support apparatus 320, or some other recipient, occurs in response to cessation of the movement of mobile IV stand 48 for longer than a predetermined time period. In other embodiments, transmission occurs in response to the activation of a switch or button on the mobile IV stand, or on person support apparatus 320. In still other embodiments, transmission occurs when the patient removes his or her hand from any area of sensing unit 66 for a time period exceeding a predetermined threshold. Still other triggers for the transmission of this data may also be used, either alone or in combination with any of the aforementioned triggers.

Whether mobile device 40 is implemented as an activity tracker or as a mobile IV stand, it includes, in at least one embodiment, data sufficient to enable it to be associated with a specific person support apparatus. Such association works in the same manner as has been described above with respect to first and second person support apparatus 120 and 220.

Generally speaking, mobile device 40 includes identification data that distinguishes it from other mobile devices 40. Further, when a specific person support apparatus 320 is associated with a specific mobile device 40, the unique ID of the specific mobile device is communicated to person support apparatus 320 so that communication between that specific person support apparatus 320 and that specific mobile device 40 can take place, even in the presence of other mobile devices 40 and/or person support apparatuses 320. In this manner, if a room 38, for example, includes two person support apparatuses 320 and each of the patients assigned to these two person support apparatuses has his or her own associated mobile device 40, data from the first mobile device 40 will not be transmitted to the second person support apparatus 320, or vice versa, and data from the second mobile device 40 will not be transmitted to the first person support apparatus 320, or vice versa. Instead, data from the first mobile device 40 will be correctly transmitted to the first person support apparatus 320, and data from the second mobile device 40 will be transmitted to the second person support apparatus 320.

Figure 7:
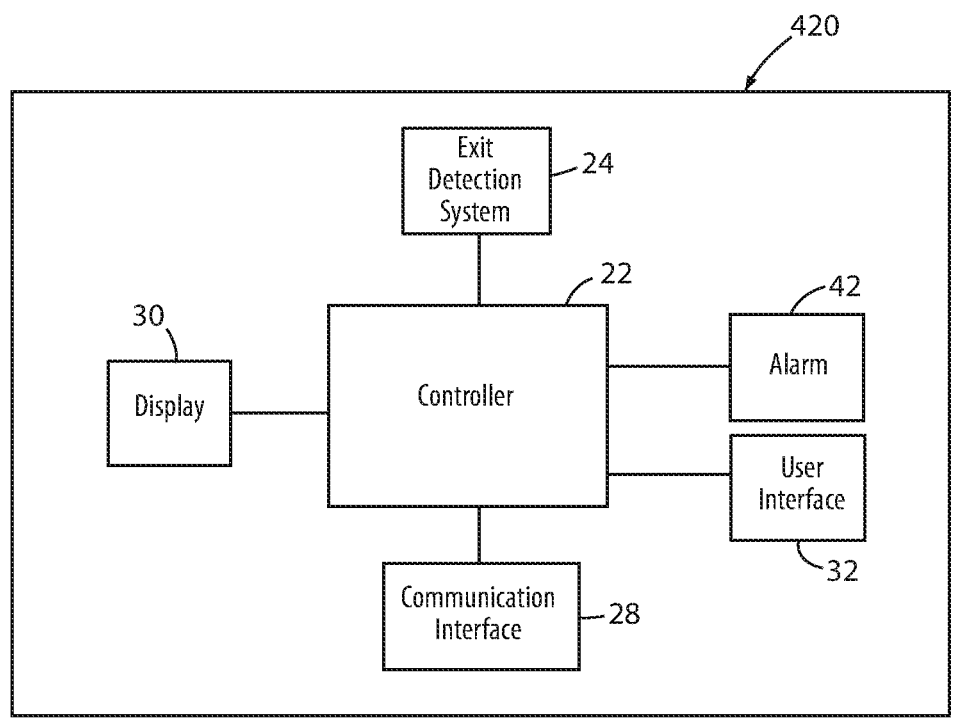
FIG. 7 is a diagram of a person support apparatus according to yet another embodiment.

FIG. 7 illustrates a modified person support apparatus 420 according to another embodiment. Person support apparatus 420 includes many of the same components of person support apparatus 20 shown in FIG. 1. However, person support apparatus 420 differs from person support apparatus 20 in that it includes an alarm 42 in communication with controller 22. Alarm 42, in at least one embodiment, includes at least one light and at least one sound-generating mechanism, such as, but not limited to, a beeper, a buzzer, and/or a speaker. Communication interface 28 is adapted, in at least one embodiment, to communicate with a nurse call system (not shown) that is installed within the facility in which person support apparatus 420 is used. Controller 22 is further configured to enable a user to select how it will react when an alarm condition is present. That is, user interface 32 allows a user to select whether an alarm condition will result in only a local alarm (i.e. activation of alarm 42), only a remote alarm (i.e. transmission of an alarm message to the nurse call system), both a local and remote alarm, or neither a local nor remote alarm.

Person support apparatus 420 is also configured to provide two different types of alarms having different priority levels, both of which relate to movement of an occupant. These two different priority levels are more easily understood with respect to FIGS. 8 and 9. Although FIGS. 8 and 9 illustrate person support apparatus 420 implemented as a recliner, it will be understood that this is done merely for purposes of illustration and that person support apparatus 420 can take on any of the other forms discussed herein. Person support apparatus 420 is adapted to allow a user to select whether to arm or disarm an alerting feature of exit detection system 24. When exit detection system 24 is armed, controller 22 activates alarm 42 when an occupant 44 leaves person support apparatus 420. When exit detection system 24 is disarmed, controller 22 does not activate alarm 42 when an occupant 44 leaves person support apparatus 420. Whether armed or disarmed, exit detection system 24 detects the departure and arrival of occupant 44. That is, the arming and disarming of exit detection system 24 refers to the arming and disarming of alarm 42 in response to an occupant's departure, and not necessarily to the functionality of the one or more sensors used in the exit detection system that detect the presence/absence of the occupant.

Person support apparatus 420 is configured such that when occupant 44 leaves person support apparatus 420, the alarm 42 activated by controller 22 will be a low priority alarm. Controller 22 is also configured to switch alarm 42 to a higher priority alarm if, after leaving person support apparatus 420, occupant 44 falls. Person support apparatus 420 therefore issues a first low priority alarm when an occupant leaves, and issues a second higher priority alarm if, after leaving, the occupant falls down.

In at least one embodiment, the first and second priority alarms meet the criteria set for by the International Electrotechnical Commission (IEC) of Geneva, Switzerland, in standard 60601-1-8 (any edition), which is incorporated herein by reference in its entirety. More specifically, controller 22 is configured to activate alarm 42 in accordance with the criteria for a low priority alarm of IEC standard 60601-1-8 when occupant 44 leaves person support apparatus 420. Controller 22 is also configured to activate alarm 42 in accordance with the criteria for a medium priority alarm of IEC standard 60601-1-8 when person support apparatus 420 detects that occupant 44 has fallen. These criteria include limitations on the color and/or brightness of the lights, as well as the volume and/or pitch of the sounds, that are emitted by alarm 42 for each priority level of the alarm.

Communication interface 28 of person support apparatus 420 is configured to communicate with a mobile fall detection device 46 (FIGS. 8-9) that is adapted to be worn by an occupant 44 of person support apparatus 420. Such communication provides person support apparatus 420 with information regarding whether or not occupant 44 has fallen. In some embodiments, communication between communication interface 28 and fall detection device 46 takes place via a WiFi (IEEE 802.01) link. In other embodiments, different types of wireless links may be used, such as, but not limited to, ZigBee, Bluetooth, etc.

Fall detection device 46, in at least some embodiments, is a commercially available wristband, bracelet, necklace, or other type of structure adapted to be worn by an occupant 44. Fall detection device 46 includes sensors, such as one or more accelerometers, that detect downward movement of occupant 44 and hence falls. As noted previously, in some embodiments, fall detection device is any one of the previously described activity trackers that include accelerometers, or other sensors, adapted to detect a person's fall. Regardless of its physical form, fall detection device 46 includes a communication transceiver that enables it to communicate a fall message to communication interface 28 when it detects that occupant 44 has fallen. Upon receipt of such a fall message, controller 22 escalates the priority status of alarm 42 from a first priority level to a higher priority level.

Fall detection device 46 includes a unique identifier, in at least one embodiment, that enables it to be paired or associated with a specific person support apparatus 420. Such pairing ensures that when fall detection device 46 detects an occupant fall, the fall message it transmits will be directed to the appropriate person support apparatus 420 (i.e. the one that the occupant exited). Any other person support apparatuses 420 that may be within communication range of fall detection device 46 and who might detect the fall message will not react to the fall message because they are not associated with that specific fall detection device 46. Such association takes place, in at least one embodiment, by manually entering information identifying the specific fall detection device 46 into the memory of person support apparatus 420 using user interface 32.

In some embodiments, fall detection device 46 includes a unique bar code and user interface 32 includes a bar code reader that reads the bar code. After reading the bar code, person support apparatus 420 only responds to fall messages sent from the specific fall detection device having that particular bar code, or an ID associated with that particular bar code. The fall message sent by fall detection device 46 includes the bar code, or the ID associated with that bar code, so that controller 22 can determine whether any fall messages received by communication interface 28 are to be processed or ignored.

In other embodiments, fall detection device 46 includes an electronic tag, such as a near field communication transceiver, or other type of electronic tag that is detectable by one or more sensors on person support apparatus 420 when positioned within a close proximity to person support apparatus 420. In these embodiments, controller 22 is configured to automatically associate itself with the specific fall detection device 46 when it is within communication range (i.e. occupant 44 is sitting or lying on person support apparatus 420) of the fall detection device 46. Other manners for associating a specific fall detection device 46 with a specific person support apparatus 420 are also possible.

Controller 42 is configured, in at least some embodiments, to ignore fall messages that may be transmitted from fall detection device 46 while the occupant is still supported on person support apparatus 420. That is, in some instances, it is possible that an occupant's movement while positioned on person support apparatus 420 may trigger a false fall message from fall detection device 46. This may result from the occupant lying down on person support apparatus 420 (especially if it is a bed), or otherwise shifting his or her body in a way that involves sharp accelerations, or other types of movements, that trigger fall detection device 46. Controller 22 does not issue a higher priority alarm, or any alarm at all, in these situations, because controller 22 has not received a signal or message from exit detection system 24 of person support apparatus 420 indicating that the occupant has exited person support apparatus 420. Instead, with the occupant still on person support apparatus 420, controller 22 interprets any fall message it receives as incorrect and takes no alerting action. Only after the occupant leaves person support apparatus 420—which is detected by exit detection system 24—does controller 22 respond to a received fall message by escalating the low priority alarm, due to the occupant's departure from person support apparatus 420, to a higher priority alarm.

Person support apparatus 420 is configured, in some embodiments, to only activate a higher priority alarm when the lower priority alarm has first been activated. That is, in some embodiments of person support apparatus 420, controller 22 does not issue any alarm based on a fall message from fall detection device 46 unless exit detection system 24 has detected a patient's exit and controller 22 has activated alarm 42 to its first priority. Only after alarm 42 have been activated to a first priority level will controller 22 escalate this alarm to a higher priority level if a fall message is received.

In still other embodiments, person support apparatus 420 is configured to allow a user to choose whether to issue an alarm in response to an occupant fall independently of whether or not an alarm is issued upon an occupant's departure from person support apparatus. In other words, in this embodiment, person support apparatus 420 can be configured to not issue an alarm when the occupant leaves person support apparatus 420, but to issue an alarm thereafter if a fall is detected. In such an embodiment, controller 22 still utilizes inputs from exit detection system 24 when determining whether a fall message received from fall detection device 46 is valid or not, as discussed previously.

That is, if controller 22 receives a fall message from fall detection device 46 while exit detection system 24 is still detecting the presence of the occupant on person support apparatus 420, controller 22 interprets this as an invalid fall message and does not activate alarm 42. This helps reduce false fall alarms.

In some embodiments, fall detection device 46 is not implemented as a mobile device that is worn by occupant 44. In such embodiments, the detection of an occupant's fall is determined by other means. For example, in one embodiment, person support apparatus 420 includes one or more thermal cameras positioned thereon that capture thermal images of the areas surrounding person support apparatus 420. These images are analyzed by controller 22 to detect the presence and location of occupant 44 when occupant 44 is positioned off person support apparatus 420. If the height and/or position of the occupant's body detected in the thermal images changes in a manner indicative of a fall, controller 22 activates and/or escalates alarm 42 in the manners discussed above. One example of a person support apparatus that incorporates such thermal image sensors for detecting an occupant's fall is disclosed in more detail in commonly assigned U.S. patent application Ser. No. 61/989,243 filed May 6, 2014 by inventors Marko N. Kostic et al. and entitled PERSON SUPPORT APPARATUS WITH POSITION MONITORING, the complete disclosure of which is hereby incorporated herein by reference.

In other embodiments, fall detection device 46 is implemented using one or more visual cameras positioned on person support apparatus 420 and/or within the vicinity of person support apparatus 420. These cameras capture visual images of person support apparatus 420 and the areas surrounding person support apparatus 420 (e.g. room 38). The visual images are processed, such as by controller 22 or another controller, and analyzed to determine if occupant 44 has fallen after leaving person support apparatus 420. One example of such a visual image detection system that can be used to implement fall detection device 46 is disclosed in the aforementioned Ser. No. 13/242,022 patent application, which has already been incorporated herein by reference. In some embodiments, when fall detection device 46 is implemented as a video monitoring system, such as that disclosed in the Ser. No. 13/242,022 patent application, the video monitoring system may also perform the function of exit detection system 24. In such embodiments, both fall detection device 46 and exit detection system 24 utilize the same hardware and are effectively combined into a single system. In other embodiments, person support apparatus 420 retains its own exit detection system 24 that is separate from the video monitoring system used to implement fall detection device 46.

In still other embodiments, person support apparatus 420 includes its own fall detection device—such as a thermal image sensor of the type disclosed in the aforementioned 61/989,243 patent application or some other type—but is adapted to transmit a fall detection message to another person support apparatus rather than issuing and/or escalating the priority of an existing alarm. The person support apparatus that receives the fall detection message from person support apparatus 420 then either issues an alarm or escalates an existing alarm to a higher priority. The person support apparatus that receives the fall detection message may include its own fall detection sensors. By including fall detection sensors in multiple person support apparatuses that are in communication with each other, a greater range for detecting falls can be obtained. Thus, for example, in a room of a medical facility that includes two or more person support apparatuses 420 that each have their own fall detection devices, a patient who exits a first one of the person support apparatuses 420 and walks outs of range of the fall detector of the first person support apparatus 420 may still be in range of a fall detector of the second person support apparatus. When the second person support apparatus 420 detects this fall, it forwards a fall message to the first person support apparatus 420, which is the person support apparatus associated with the patient. The second person support apparatus 420 that detects the fall is, in some embodiments, also associated with the patient. In other embodiments, the second person support apparatus 420 is associated with a different patient, or not associated with any patient at all.

User interface 32 enables a user to select whether the escalated alarming performed by controller 22 in response to an occupant's fall occurs only locally (i.e. at person support apparatus 420), occurs only remotely (e.g. at a nurses' station in a hospital), or occurs both locally and remotely. Based on this selection, controller 22 determines whether to activate alarm 42 in response to an occupant's fall, whether to transmit a message to communication interface 28 for communication to a remote device (e.g. a nurse call system), or whether to do both.

Communication interface 28, in at least one embodiment, is configured to send a message wirelessly to a nurse call system indicating that alarm 42 has been activated, as well as an indication of whether the alarm is at the higher or the lower priority level. In one embodiment, this wireless communication with the nurse call system is carried out in any one of the manners disclosed in commonly assigned U.S. patent application Ser. No. 62/035,656 filed Aug. 11, 2014 by inventors Krishna S. Bhimavarapu et al. and entitled PATIENT SUPPORT APPARATUSES WITH WIRELESS HEADWALL COMMUNICATION, the complete disclosure of which is incorporated herein by reference. If fall detection device 46 is configured to be worn by occupant 44 (rather than implemented as a visual or thermal image system), then communication interface 28 also includes hardware and programming enabling it to communicate wirelessly with fall detection device 46. In some embodiments, communication interface 28 includes the same hardware and uses the same protocols for communicating with fall detection device 46 and the nurse call system, such as, but not limited to, WiFi, Bluetooth, and/or ZigBee.

In another embodiment, communication interface 28—in addition to including hardware and programming for communicating with fall detection device 46—also includes a plurality of relays, or other electrically controlled switches, that are in electrical communication with a cable port on person support apparatus 420. When controller 22 activates alarm 42 at a first priority level and controller 22 is configured to communicate this information remotely to a nurse call system, communication interface 28 changes the state of a corresponding one of the relays (i.e. closes or opens the relay). When controller 22 activates alarm 42 at a second priority level and controller 22 is configured to communicate this information remotely to a nurse call system, communication interface 28 changes the state of second one of the relays that corresponds to this second alarm priority level.

Figure 10:
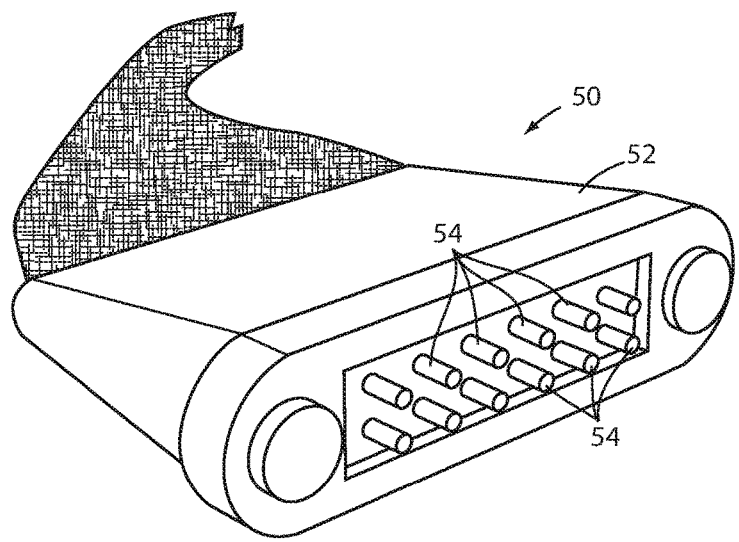
FIG. 10 is a perspective view of a portion of one type of cable that may be used with any of the person support apparatuses disclosed herein.

A cable, such as cable 50 shown in FIG. 10, connects person support apparatus 420 to a nurse call receptacle integrated into a headwall of a medical facility. Cable 50 may be a conventional nurse call cable, which typically includes 37 pins, or it may be another type of cable. In one embodiment, cable 50 is a magnetically coupled cable, such as that disclosed in commonly assigned U.S. patent application Ser. No. 13/790,762 filed Mar. 8, 2013 by inventors Krishna S. Bhimavarapu et al. and entitled PATIENT SUPPORT APPARATUS CONNECTORS, the complete disclosure of which is hereby incorporated herein by reference. Other types of cables may, of course, be used.

Regardless of the specific number of pins or specific physical configuration of cable 50, it includes a plug 52 having a plurality of pins 54. Plug 52 is adapted to be inserted into the cable port on person support apparatus 420. The other end of cable 50 (not shown) includes a plug that is adapted to be plugged into the receptacle of the nurse call system. Each pin 54 of plug 52 is adapted to fit into a corresponding receptacle on the cable port of person support apparatus 420. Each receptacle is, in turn, in electrical communication with one of the relays.

Controller 22's changing of a state of a first relay in response to a first priority alarm thereby either opens or closes an electrical pathway that extends between a first pin 54 in electrical communication with the first relay and another pin 54 corresponding to an electrical ground. Similarly, controller 22's changing of a state of a second relay in response to a second priority alarm thereby either opens or closes an electrical pathway that extends between a second pin 54 in electrical communication with the second relay and the electrical ground pin. The result is that the nurse call system is able to detect the changes in the relay states on person support apparatus 420 when the nurse call cable is connected between the port on person support apparatus 420 and the nurse call receptacle. The nurse call system can thereby determine if either a first or second level priority alarm has been activated.

FIG. 11 illustrates one example of a person support apparatus 520 that is implemented as a hospital bed. It will be understood that any of person support apparatuses 20, 120, 220, 320, and/or 420 discussed herein can be physically constructed in a similar manner to the construction of person support apparatus 520. Person support apparatus 520 includes a base 80 having a plurality of wheels 82, a pair of lifts 84 supported on the base, a frame or litter 86 supported on the lifts 84, and a support deck 88 supported on the frame 86. Lifts 84 are adapted to raise and lower frame 86 with respect to base 80, either in unison or in a manner that allows tilting of frame 86 with respect to horizontal.

Support deck 88 provides a support surface 90 on which a mattress (not shown), or other soft cushion is positionable so that a person may lie and/or sit thereon. Support deck 88 is made of a plurality of sections, some of which are pivotable about generally horizontal pivot axes. In the embodiment shown in FIG. 11, support deck 88 includes a head section 92, a seat section 94, a thigh section 96, and a foot section 98. Head section 92, which is also sometimes referred to as a Fowler section, is pivotable about a generally horizontal pivot axis between a generally horizontal orientation (not shown in FIG. 11) and a plurality of raised positions (one of which is shown in FIG. 11). Thigh section 96 and foot section 98 may also be pivotable.

A plurality of siderails 100 (FIG. 11) may also be coupled to frame 86. Siderails 100 are movable between a raised position in which they block ingress and egress into and out of person support apparatus 520, and a lowered position in which they are not an obstacle to such ingress and egress.

The construction of any of base 80, lifts 84, frame 86, support deck 88, and/or siderails 100 may take on any known or conventional design, such as, for example, that disclosed in commonly assigned, U.S. Pat. No. 7,690,059 issued to Lemire et al., and entitled HOSPITAL BED, the complete disclosure of which is incorporated herein by reference; or that disclosed in commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosure of which is also hereby incorporated herein by reference. The physical construction of person support apparatus 520 can also take on different forms from what is disclosed in the aforementioned patent and patent publication.

As noted previously, any of person support apparatuses 20, 120, 220, 320, and/or 420 can take on other forms besides beds, such as bed 520 of FIG. 11. One other type of form that person support apparatuses 20, 120, 220, 320, and/or 420 can take on is a chair or recliner. When implemented as a chair or recliner, any of these person support apparatuses may be physically constructed in any of the manners disclosed in commonly assigned U.S. patent application Ser. No. 14/212,323 filed Mar. 14, 2014 by inventors Christopher Hough et al. and entitled MEDICAL SUPPORT APPARATUS, the complete disclosure of which is hereby incorporated herein by reference. Person support apparatuses 20, 120, 220, 320, and/or 420 can also take on different forms.

It will be understood by those skilled in the art that any of the features of any one of the person support apparatuses discussed herein (20, 120, 220, 320, 420, and/or 520) can be combined with any of the features of any other one of these person support apparatuses. Thus, for example, person support apparatus 420, in addition to escalating an alarm priority level when a patient fall is detected, can be configured to monitor the time a patient spends off person support apparatus 420 (similar to person support apparatus 20); and/or to communicate with a second person support apparatus (similar to person support apparatuses 120 and 220); and/or to communicate with a mobile device 40, such as an activity tracker or a mobile IV stand, or the like (similar to person support apparatus 320).

Any of person support apparatuses 20, 120, 220, 320, 420, and/or 520 can also be configured to carry out any one or more of the functions described herein (e.g. calculating an occupant's mobility time; tracking how many steps an occupant takes; escalating a priority level of an alarm, etc.) by utilizing one or more software applications that are downloaded from, and/or executed in conjunction with, a network service in the manners disclosed in commonly assigned PCT patent publication WO 2014/150970 filed Mar. 12, 2014 by applicant Stryker Corporation and entitled PATIENT SUPPORT APPARATUS WITH REMOTE COMMUNICATION, the complete disclosure of which is hereby incorporated herein by reference. Thus, for example, person support apparatus 20, 120, 220, 320, 420, and/or 520 can be initially installed in a facility with the hardware shown in FIG. 1 and/or FIG. 7, but not include the necessary software for carrying out one or more of the functions described herein. Communication interface 28, however, is adapted to couple to a computer network having one or more network services that transmit the necessary software application to the person support apparatus to carry out one or more of these functions. The transmitted software application is, in some embodiments, a thin or thick client application that operates in conjunction with the network service, or it may be a standalone application that operates completely independently of the computer network.

In still other embodiments, the software applications that carry out any one or more of the functions described herein may be accessible from an on-line app store for person support apparatuses. Controller 22 has access to this app store via communication interface 28. The downloading and/or usage of such apps by a particular person support apparatus 20, 120, 220, 320, 420, and/or 520 results in a bill to the medical facility for that particular download and/or usage. Such customized billing and configurability for person support apparatuses is disclosed in more detail in commonly assigned U.S. patent application Ser. No. 62/081,744 filed Nov. 19, 2014 by inventors Daniel Brosnan et al. and entitled MEDICAL APPARATUS WITH SELECTIVELY ENABLED FEATURES, the complete disclosure of which is hereby incorporated herein by reference. A medical facility using any of person support apparatuses 20, 120, 220, 320, 420, and/or 520 can therefore download an app allowing the person support apparatus to monitor a patient's time out of bed; to communicate with other person support apparatuses; to communicate with a mobile IV stand; to communicate with an activity tracker; to detect patient falls; and/or to escalate alarm priorities in response to a detected patient fall.

Any one of person support apparatuses 20, 120, 220, 320, 420, and/or 520 can be further modified to issue an exit alarm based upon an occupant exiting a different person support apparatus. In such situations, the exiting of the person from a first person support apparatus is detected by exit detection system 24 of the first person support apparatus. The first person support apparatus then sends an exit message via its communication interface 28 to the communication interface 28 of a second person support apparatus. The second person support apparatus then issues an alarm indicating that the person has exited from the first person support apparatus. Further, if the person subsequently falls and it is detected by a fall detection device 46 on the first person support apparatus, the first person support apparatus transmits a fall message to the second person support apparatus and the second person support apparatus, if so configured, escalates the alarm from a lower priority level (corresponding to the person's exiting from the first person support apparatus) to a higher priority level (corresponding to a fall).

The aforementioned modified person support apparatuses can be implemented, as one example, as a bed and a recliner that are associated with a specific patient in a medical facility. If the patient is seated in the recliner and its exit detection system is armed, the recliner transmits an exit detection message to the bed associated with that patient. The bed then issues an exit alarm. The recliner may or may not issue its own alarm, depending upon its configuration. If the bed and recliner both include fall detection sensors, and the recliner subsequently detects that the patient has fallen, it sends a fall message to the bed. The bed then escalates the exit alarm to a fall alarm. Depending upon how the user of the bed has configured the bed via user interface 32, the bed also forwards alarm signals to a remote location (e.g. a nurse call system) for the patient's exit from the recliner and/or for the patient's fall.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A person support apparatus comprising:
    a support surface adapted to support a person thereon;
    an exit detector adapted to issue an alarm if the person exits the support surface;
    a fall detection sensor integrated into the person support apparatus, the fall detection sensor adapted to detect if the person falls; and
    a controller in communication with the exit detector and the fall detection sensor, the controller adapted to issue a first alarm if the person exits the support surface and to issue a second alarm if the person falls, the second alarm having a higher priority than the first alarm, and wherein both the first and second alarms are communicated by the controller to a remote location.

2. The person support apparatus of claim 1 wherein the exit detector comprises a plurality of load cells positioned to support the support surface.

3. The person support apparatus of claim 1 wherein the first alarm includes both a visual and an audio component.

4. The person support apparatus of claim 1 wherein the fall detection sensor comprises an image sensor adapted to detect images of the person after he or she exits from the person support apparatus.

5. The person support apparatus of claim 4 wherein the image sensor is a thermal image sensor.

6. The person support apparatus of claim 1 wherein the remote location includes a nurse call system, and wherein the person support apparatus further comprises a cable interface adapted to releasably couple to a cable of the nurse call system, the cable interface including a plurality of electrical connectors, and wherein the controller is adapted to open or close a first switch in communication with a first one of the electrical connectors when issuing the first alarm and to open or close a second switch in electrical communication with a second one of the electrical connectors when issuing the second alarm.

7. The person support apparatus of claim 1 wherein the remote location includes a local area network and the person support apparatus further comprises a wireless interface adapted to wirelessly communicate with the local area network, and the controller is further adapted to send a first message to the local area network via the wireless interface when issuing the first alarm, and to send a second message to the local area network via the wireless interface when issuing the second alarm.

8. The person support apparatus of claim 1 wherein the person support apparatus is one of a bed, stretcher, and chair.

9. A person support apparatus system comprising:
    a first person support apparatus comprising a first support surface, an exit detector, and a first controller;
    a second person support apparatus comprising a second support surface, a fall detection sensor integrated into the second person support apparatus, and a second controller; and
    wherein the first person support apparatus is in communication with the second person support apparatus and the first controller is adapted to issue a first alarm if a person exits the first person support apparatus, and the first controller is further adapted to issue a second alarm if the fall detection sensor detects a fall of the person.

10. The person support apparatus system of claim 9 wherein the first person support apparatus further comprises a fall detection sensor and the first controller is further adapted to issue the second alarm if the fall detection sensor of the first person support apparatus detects the fall of the person.

11. The person support apparatus system of claim 9 wherein the first person support apparatus is a bed and the second person support apparatus is a chair.

12. The person support apparatus system of claim 9 wherein the second controller is also adapted to issue the second alarm if the fall detection sensor detects the fall of the person.

13. The person support apparatus system of claim 12 wherein the second controller is further adapted to issue the first alarm if the exit detector detects the person exiting the first person support apparatus.

14. The person support apparatus system of claim 9 wherein the second person support apparatus further comprises exit detector adapted to detect if the person exits the second person support apparatus.

15. The person support apparatus system of claim 14 wherein the first controller is further adapted to issue the first alarm if the exit detector of the second person support apparatus detects the person exiting the second person support apparatus.

16. The person support apparatus system of claim 9 further comprising a cable interface adapted to releasably couple to a cable of a nurse call system, the cable interface including a plurality of electrical connectors, and wherein the first controller is adapted to open or close a first switch in communication with a first one of the electrical connectors when issuing the first alarm and to open or close a second switch in electrical communication with a second one of the electrical connectors when issuing the second alarm.

17. The person support apparatus system of claim 9 wherein the first person support apparatus further includes a first ID and the second person support apparatus further includes a second ID, wherein the first person support apparatus is configured to transmit the first ID to the second person support apparatus and the second person support apparatus is configured to transmit the second ID to the first person support apparatus.

* * * * *